United States Patent
Mendonca

[11] Patent Number: 6,110,156
[45] Date of Patent: Aug. 29, 2000

[54] OSTOMY BAG GARMENT

[76] Inventor: Ilona Mendonca, Five Hillwood Pl., Norwalk, Conn. 06850

[21] Appl. No.: 09/192,786

[22] Filed: Nov. 16, 1998

[51] Int. Cl.⁷ ...................................................... A61F 5/44
[52] U.S. Cl. ............................................................ 604/345
[58] Field of Search ................................. 604/332, 345, 604/349; 2/211, 400–408, 247–253, 238, 228, 227, 114

[56] References Cited

U.S. PATENT DOCUMENTS

| | | | |
|---|---|---|---|
| 2,778,362 | 1/1957 | Pollock et al. | 128/283 |
| 3,421,505 | 1/1969 | Freeman et al. | 128/283 |
| 3,468,310 | 9/1969 | Kimball | 128/283 |
| 3,547,123 | 12/1970 | Sachs | 128/295 |
| 4,495,662 | 1/1985 | Miller | 2/211 |
| 4,511,358 | 4/1985 | Johnson, Jr. et al. | 604/327 |
| 4,513,455 | 4/1985 | Gerhardt | 2/253 |
| 4,533,355 | 8/1985 | Fair | 604/345 |
| 4,666,432 | 5/1987 | McNeisch et al. | 604/174 |
| 4,820,291 | 4/1989 | Terauchi et al. | 604/349 |
| 4,888,006 | 12/1989 | Beaupied | 604/345 |
| 5,009,649 | 4/1991 | Goulter et al. | 604/351 |
| 5,032,118 | 7/1991 | Mason | 604/349 |
| 5,048,122 | 9/1991 | Prieur | 2/69 |
| 5,135,519 | 8/1992 | Helmer | 604/332 |
| 5,135,520 | 8/1992 | Beaupied | 604/345 |
| 5,142,702 | 9/1992 | Piloian | 2/102 |
| 5,174,305 | 12/1992 | Childs | 128/846 |
| 5,293,840 | 3/1994 | Wedlick | 119/850 |
| 5,626,570 | 5/1997 | Gallo | 604/345 |
| 5,643,233 | 7/1997 | Turner | 604/332 |
| 5,651,777 | 7/1997 | Walters | 604/345 |

FOREIGN PATENT DOCUMENTS

WO 89/06949  8/1989  European Pat. Off. .

OTHER PUBLICATIONS

Ostomy Catalog and Educational Training Manual, 11ᵗʰ Edition, 1968, United Surgical Corporation, Largo, Florida 33540, Security Pouch Colostomy After Irrigation Appliance, #2290.

*Primary Examiner*—John G. Weiss
*Assistant Examiner*—Carrie Mager
*Attorney, Agent, or Firm*—St. Onge Steward Johnston & Reens LLC

[57] ABSTRACT

A garment for an ostomy bag is provided having a layer of pocket material attached to a portion of a garment and means for securing the bag to the pocket, and a pleat.

12 Claims, 3 Drawing Sheets

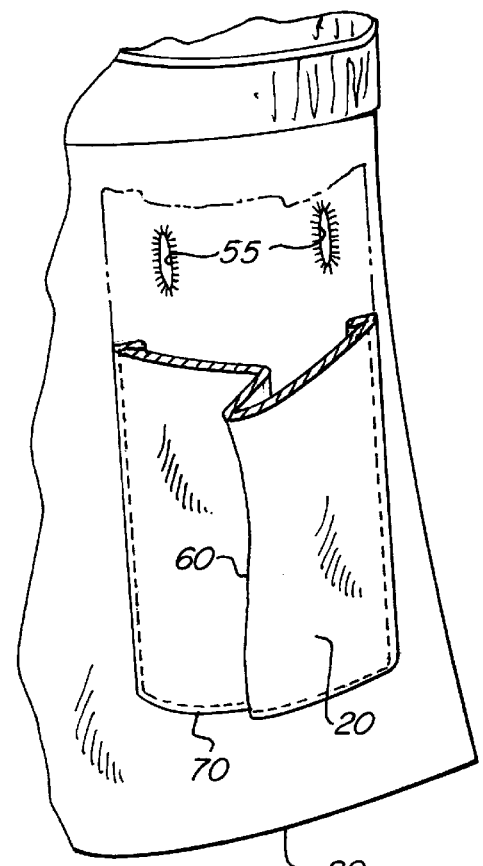
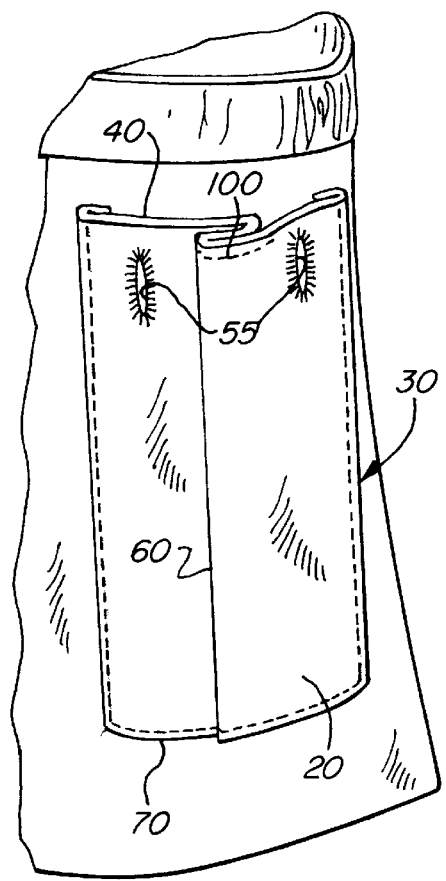
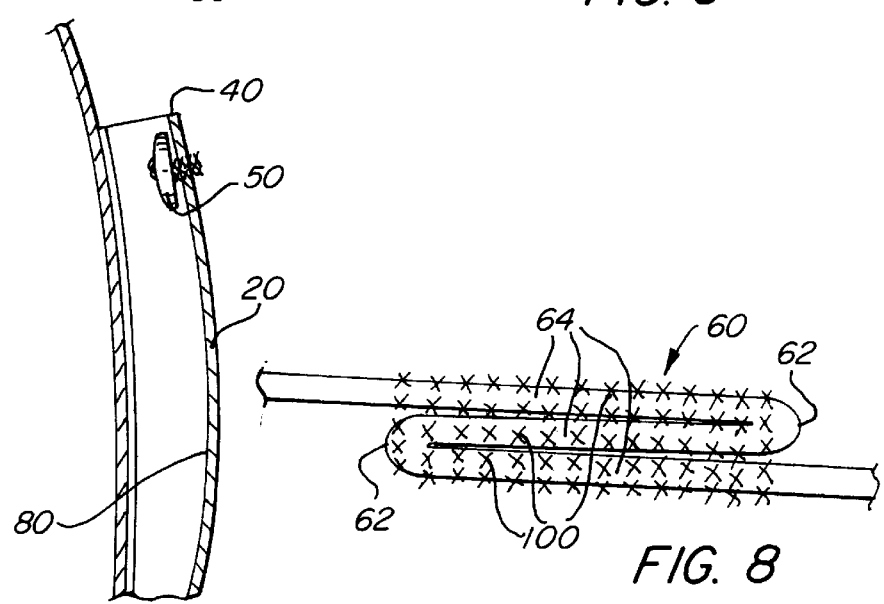
FIG. 5
FIG. 6
FIG. 7
FIG. 8

OSTOMY BAG GARMENT

FIELD OF THE INVENTION

This invention relates to ostomy bag garments, including underwear.

BACKGROUND OF THE INVENTION

Devices for securing ostomy bags to persons are known. For example a pair of rubber straps is commonly used to secure an ostomy bag to a person's leg. This approach is undesirable because the accumulation of waste material in the bag tends to be felt by the person, the skin of the person's leg tends to get hot and sweaty adjacent to the bag, and the person typically must lower her pants to the floor or remove them to empty the waste material from the bag.

In addition, at night, larger ostomy bags or night bags are typically used. These bags must be hung on a wheeled support next to the bed. This approach is undesirable because the tubing attached to the ostomy bag may constrain the person or otherwise interfere with the person's movements during sleep. In addition, the person attached to such a night bag must wheel the support with the bag to the lavatory or elsewhere should the person need to relocate Examples of devices for securing ostomy bags are found in U.S. Pat. Nos. 5,626,570 to Gallo, 5,135,519 to Helmer, 5,643,233 to Turner, 5,651,777 to Walters, 5,174,305 to Childs, and 4,666,432 to McNeish et al. A disadvantage of these devices is that they are uncomfortable to wear, tend to be difficult to apply and to remove or tend to be visible when worn.

Also known are garments having pockets with and without pocket flaps and/or pocket closures. Examples of these are U.S. Pat. Nos. 5,135,520 to Beaupied, 4,888,006 to Beaupied, 5,009,649 to Goulter et al., WO 89/06949 to Beaupied, 5,293,840 to Wedlick, 3,421,505 to Freeman et al., 2,778,362 to Pollock et al., 3,468,310 to Kimball, 4,533,355 to Fair, 5,048,122 to Prieur, 3,547,123 to Sachs, 4,495,662 to Miller, 5,142,702 to Piloian, 5,032,118 to Mason, and 4,820,291 to Terauchi et al. The '362, '355, and '662, moreover, disclose garments having holes in either the garment or the front of the pocket or both for the tubing, stoma, or ostomy appliance. Further, the '118 patent discloses a pocket that extends below the lower edge of the garment and having an opening at the lower edge of the pocket for emptying the pouch. The '291, moreover, requires that the pocket be made of special water-resistant material. To change the ostomy bag for the garment disclosed in the '118 patent, pants worn over the garment must be taken down to the ankle or removed entirely to drain the bag.

A disadvantage of these garments is bulging of the pocket, that they are uncomfortable or difficult to wear, that the bag falls down in the pocket, or that the bag does not fill properly or is otherwise restricted so as to impede the flow of the person's waste material. None of these references have a device for securing the bag and minimizing the bulging of the bag within the pocket, or pleats that allow the bag to fill. A further disadvantage of prior art garments or devices is that they are not easily manufactured in that they require special designs, materials and methods of manufacture, or they require special outerwear to accommodate the garment or device.

What is desired, therefore, is an ostomy bag garment which prevents the ostomy bag from falling down and unsightly bulging, and which allows the bag to freely fill, and can be comfortably worn throughout the night, and yet is comfortable and relatively simple to apply and remove.

SUMMARY OF THE INVENTION

Accordingly, it is an object of the present invention to provide an ostomy bag garment which is comfortable to wear, and which may be worn through the night.

Another object of this disclosure is to provide an ostomy bag garment which is simple to apply and remove, and which allows the bag to be easily emptied.

A further object of the present disclosure is to provide an ostomy bag garment which is not readily visible when worn, especially when the bag becomes full.

Yet another object of the present invention is to provide an ostomy bag garment which allows the bag to fill easily without unduly restricting the filling of the bag.

Still yet another object of the present disclosure is to provide an ostomy bag garment which does not fall down in the pocket.

These and other objects are achieved by provision of an ostomy bag garment having a layer of pocket material with upper and lower edges and inner edges, the layer being sewn to the front side portion of said underwear to form a pocket for retaining an ostomy bag, a pair of buttons attached within the pocket near the upper inner edge of said pocket material for securing the ostomy bag within the pocket to prevent the bag from falling down in the pocket, at least one pleat in said pocket material for allowing the bag to fill, and the pocket being constructed so as to allow the bag to fill while minimizing bulging of the pocket. Preferably, the garment for holding an ostomy bag has a pleat for allowing the bag to fill.

The invention and its particular features will become more apparent from the following detailed description considered with reference to the accompanying drawings.

BRIEF DESCRIPTION OF THE DRAWINGS

FIG. 5 is a partially broken away plan view of an alternate embodiment of the garment in accordance with this disclosure.

FIG. 6 is a plan view of an alternate embodiment of the garment in accordance with this disclosure.

FIG. 7 is a cross-sectional view of the garment showing an alternate embodiment in accordance with this disclosure.

FIG. 8 is an exploded view of the pleat in accordance with this disclosure.

DETAILED DESCRIPTION OF THE INVENTION

Figure 1:
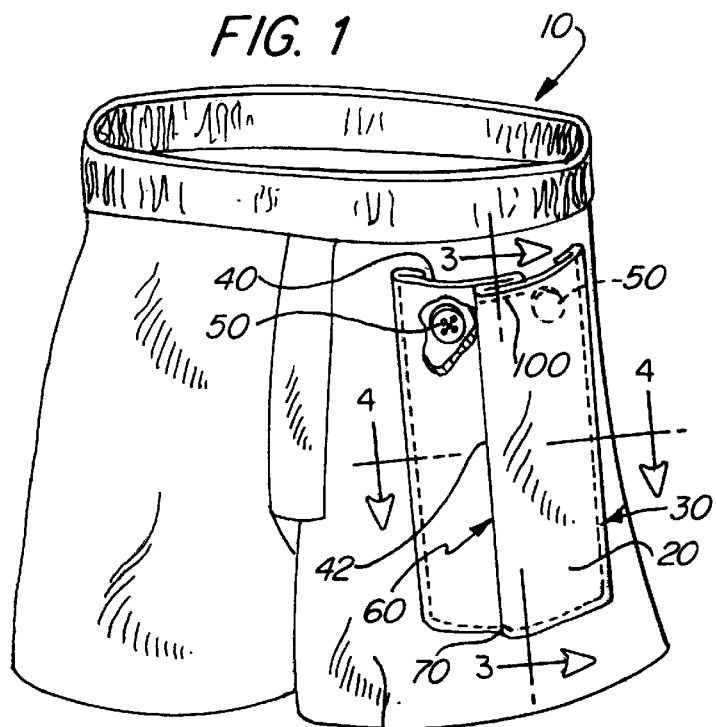
FIG. 1 is a front plan view of a garment for holding an ostomy bag.
Figure 2:
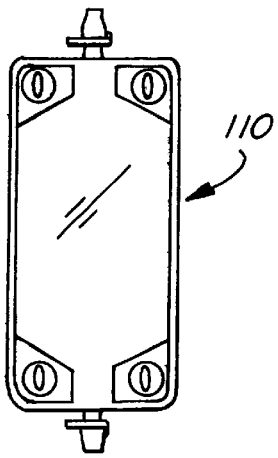
FIG. 2 is an ostomy bag.

FIG. 1 depicts a garment 10 for securing an ostomy bag 110, which is shown in FIG. 2, in accordance with the present disclosure. The garment 10 has a pocket 30 formed by a layer of pocket material 20 attached to a portion 90 of the garment 10 and a means for securing the bag 110 in the pocket 30. The means for securing the bag 110 in the pocket 30 includes buttons 50 or button holes 55, preferably, and hooks or eyes. Preferably, the buttons 50 or buttonholes 55 are at the upper edge 40 of the pocket 30, and, more preferably, are on a portion 90 of the garment 10 adjacent to the upper edge 40 of the pocket 30.

Figure 3:
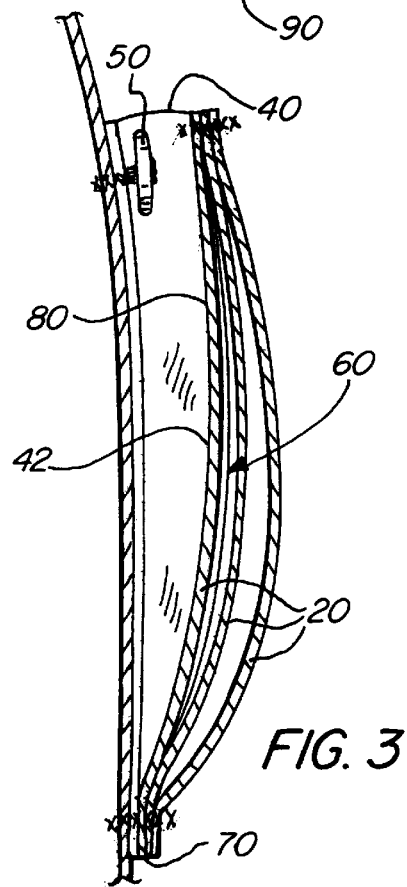
FIG. 3 is a cross-sectional view of the garment of FIG. 1 taken along section lines 3—3.

FIG. 3 is a cross-sectional view of the pocket of FIG. 1 showing the button 50 attached to the portion 90 of the garment 10. FIG. 7 shows an alternate embodiment having the button 50 attached to the inner 80, upper edge 40 of the pocket 30. FIGS. 5 and 6 depict a garment 10 having pockets 30 having button holes 55 instead of buttons 50 attached preferably to a portion 90 of the garment 10, and at the upper edge 40 of the layer of pocket material 20, respectively.

Figure 9:
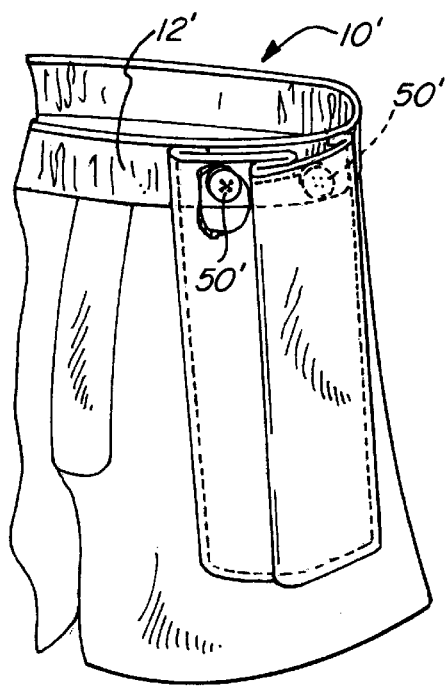
FIG. 9 is a plan view of an alternate embodiment of the garment in accordance with this disclosure.

FIG. 9 shows an even more preferred embodiment of the garment 10 in FIG. 1 where the buttons 50' are on the elastic or waistband portion 12' of the garment 10'. The garment 10' shown in FIG. 9 is preferred because it can be used to accommodate larger bags 110 used at night. It is also preferred because attaching the bag 110 to the waistband portion 12' of the garment 10' holds the hoses and the bag 110 closer to the body of the person.

Figure 10:
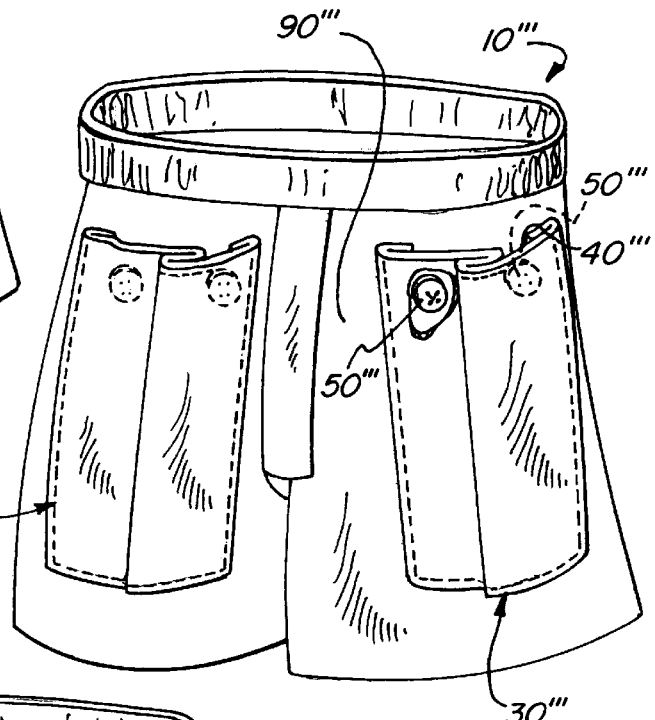
FIG. 10 is a plan view of an alternate embodiment of the garment in accordance with this disclosure.
Figure 11:
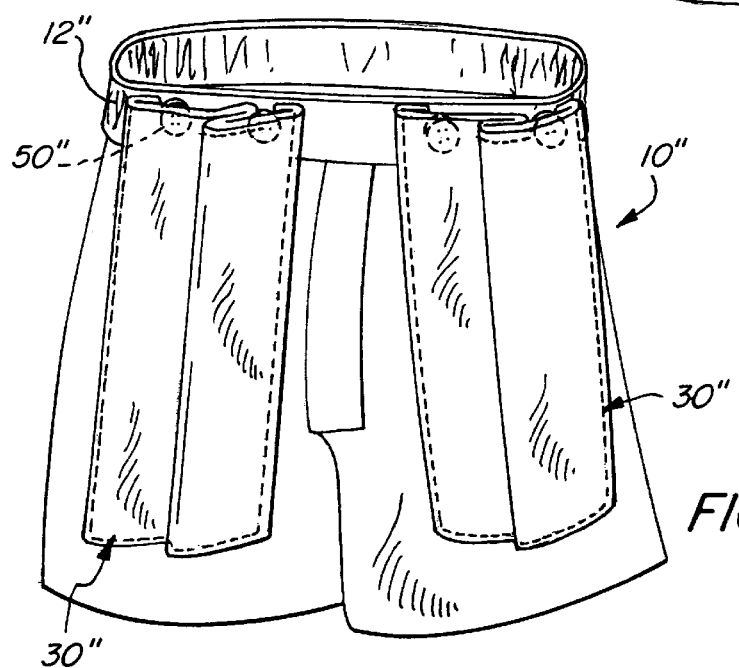
FIG. 11 is a plan view of an alternate embodiment of the garment in accordance with this disclosure.

FIGS. 10 and 11 show alternate embodiments of the garments in FIGS. 1 and 9, respectively. In FIG. 11, the garment 10" has two pockets 30" and buttons 50" on the waistband portion 12" of the garment 10". In FIG. 10, the garment 10"Δ has two pockets 30"Δ and buttons 50"Δ on a portion 90"Δ of the garment 10"Δ adjacent to the upper edge 40"Δ of the pocket 30"Δ. These garments 10" and 10"Δ may be useful for persons having two ostomies. Other combinations of pockets 30, 30', 30" and 30"Δ may be useful.

It is understood that the garment 10 includes conventional underpants, shorts, pants, bathing trunks or any other garment in which a pocket 30 may be formed. It is further understood that the pocket 30 may be on the right side or the left side or the inside or the outside or the front or the back of the garment 10, depending upon where the stoma is. Preferably, for a nephrotomy, the ostomy bag pocket 30 is on the front side portion 90 of the garment 10, as shown in FIG. 1.

The garment 10 as shown in FIG. 1 is preferably underwear without any modifications made to it except the forming of the pocket 30 with the securing means. The pocket 30 may be a rectangular pocket 30, as shown in FIG. 1, sewn to the garment 10 on three sides.

Figure 4:
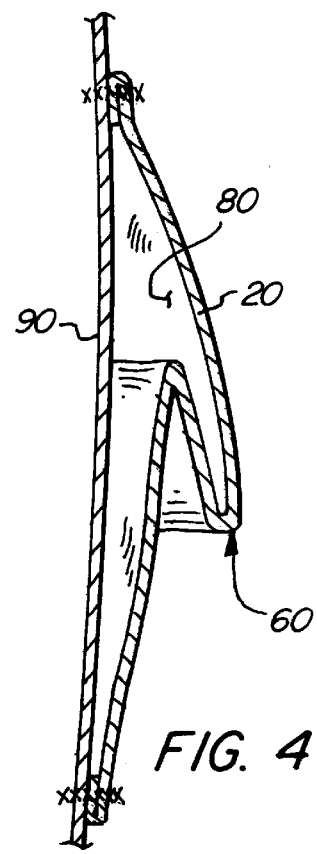
FIG. 4 is a cross-sectional view of the garment of FIG. 1 taken along section lines 4—4.

As is further shown in FIG. 1, the pocket 30 preferably has a pleat 60 for allowing the waste material to fill the ostomy bag 110. It is also understood that elastic may be substituted for the pleat 60. The pleat 60 preferably has stitching 100 or is otherwise fixed at the upper edge 40, as shown in FIGS. I and 6. It is understood that the pleat 60 may be adhered at the upper edge 40 so as to fix the pleat 60 in place at the opening 40 but allow the pleat 60 to expand when the waste material fills the bag. The pleat 60 may also be fixed at the upper edge 40 with VELCRO®, a removable plastic hook and eye attachment means. FIG. 4 is a cross-sectional view of the middle portion 42 of the pocket 30 of FIG. 1 showing the pleat 60 in further detail. FIG. 3 is another cross-sectional view of the pocket of FIG. 1 showing the upper and lower edges 40, 70 of the pocket 30 and the middle portion 42 of the pocket 30.

The preferred embodiment of the pleat 60 is shown in further detail in FIG. 8. As can be seen in FIG. 8, the pleat 60 has two folds 62 and three layers 64 of pocket material 20 held together by stitching 100 within the plane of the pocket 30. Preferably, the pleat 60 has stitching 100 at the upper and lower edges 40 and 70 of the pocket 30. The middle portion 42 has folds 62 and three layers 64 but it not stitched 100 so that the pocket 30 lays relatively flat when the bag 110 is empty, yet freely expands when the bag 110 fills so as not to unduly restrict the flow of waste material.

The garment 10 is made in accordance with the skill in the art for manufacturing underpants similar to boxer shorts. The layer of pocket material 20 may be stitched on the garment 10 or may be applied with adhesive or other attachment means so long as the pocket 30 is formed as described above. The layer of pocket material 20 is typically attached to a portion 90 of the garment 10 at the lower edge 70 without an opening therein. It is understood, however, that the pocket 30 may be removable so as to facilitate mass production of the garment 10, or so that the pocket material 20 may be applied to conventional underpants by the end user. This can be achieved using a VELCRO®, a removable plastic hook and eye attachment means.

The garment 10 and layer of pocket material 20 are preferably made of a fabric that is loose fitting to the body, and adsorptive. It is understood, however, that the layer of pocket material 20 may be any material that is flexible enough to be worn, and that can be manufactured using conventional underwear manufacturing techniques. It is also understood, however, that the layer of pocket material 20 and pocket 30 thereformed may be made of a plastic material or plastic coated fabric that can be adhered and/or thermo-formed so as to attach to the garment 10. It is also understood that any synthetic apparel material may be used for either the garment 10 or the layer of pocket material 20. Preferably, the garment 10 and the layer of pocket material 20 are made of traditional underpant material, such as a woven cotton or cotton/polyester blend fabric.

Garments 10 in accordance with this disclosure are used by persons having ostomies. An ostomy bag 110 is connected to tubing attached to a person's stoma. The bag 110 is placed in the pocket 30 with the end of the bag connected to the tubing adjacent to the upper edge 40 of the pocket 30. The bag 110 is then secured adjacent to the upper edge 40 of the pocket 30. When the bag 110 is full, the person removes the bag 110 by unsecuring the bag 110 from the pocket 30 and sliding is upward out of the pocket 30, and discharging the waste material from the lower end of the bag 110. The bag 110 is then placed back in the pocket 30 with the upper end connected to the tubing and the lower end inserted in the pocket 30. The upper end of the bag 110 is re-secured to the pocket 30.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A garment having a portion for securing an ostomy bag, comprising:
   at least one pocket attached to the garment, the at least one pocket having
      an upper edge formed from at least one layer of pocket material and a portion of said garment,
      a means adjacent to the upper edge for securing the ostomy bag in said pocket, and
      at least one pleat formed in said pocket material for allowing the bag to fill, said pleat having stitching at the upper edge.

2. The garment according to claim 1 wherein said securing means is a device selected from the group consisting of buttons, button holes, hooks and eyes.

3. The garment according to claim 2 wherein the securing means is buttons.

4. The garment according to claim 2 wherein said securing means is button holes.

5. The garment according to claim 1 wherein the portion of said garment is the front side portion.

6. The garment according to claim 1 further comprising two pockets.

7. The garment according to claim 1 wherein the pleat has two folds and three layers of the pocket material formed in the plane of said pocket, and stitching at the upper edge of said pocket.

8. An underwear having a front side portion for securing an ostomy bag, comprising:

at least one layer of pocket material having upper edge, lower edge and side edges, said lower edge and side edges sewn to a front side portion of said underwear to form at least one pocket for retaining said ostomy bag;

at least one pair of buttons attached within the pocket near the upper edge of said pocket material for securing said ostomy bag within the pocket to prevent the bag from falling down in the pocket; and at least one pleat in said pocket material for allowing said bag to fill.

9. The underwear according to claim 8 wherein said pleat has stitching at the upper edge of the pocket.

10. The underwear according to claim 8 wherein said pleat further comprises two folds and three layers of said pocket material formed in the plane of the pocket and having stitching at the upper edge and lower edge of the pocket.

11. An underwear having a waistband and front side portion for securing an ostomy bag, comprising:

at least one layer of pocket material having upper edge, lower edge and side edges, said lower edge and side edges sewn to a front side portion of said underwear to form at least one pocket for retaining an ostomy bag;

at least one pair of buttons attached to the waistband near the upper edge of said pocket material for securing the ostomy bag within the pocket to prevent the bag from falling down in the pocket; and at least one pleat in said pocket material for allowing the bag to fill, said pleat having two folds, and three layers of said pocket material formed in the plane of the pocket, and having stitching at the upper edge and lower edge of the pocket.

12. The underwear according to claim 11 wherein said underwear has two pockets each on a front side portion of said underwear.

\* \* \* \* \*